(12) United States Patent
Kamp et al.

(10) Patent No.: US 9,068,167 B2
(45) Date of Patent: Jun. 30, 2015

(54) CARDIAC DIFFERENTIATION OF HUMAN PLURIPOTENT STEM CELLS UNDER DEFINED CONDITIONS USING MATRIX OVERLAY METHODS

(75) Inventors: Timothy J. Kamp, Madison, WI (US); Sean Palecek, Verona, WI (US); Jianhua Zhang, Madison, WI (US); Samira Azarin, Madison, WI (US); Xiaojun Lian, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 468 days.

(21) Appl. No.: 12/946,019

(22) Filed: Nov. 15, 2010

(65) Prior Publication Data

US 2011/0142935 A1    Jun. 16, 2011

Related U.S. Application Data

(60) Provisional application No. 61/261,054, filed on Nov. 13, 2009.

(51) Int. Cl.
*C12N 5/00* (2006.01)
*C12N 5/077* (2010.01)

(52) U.S. Cl.
CPC .......... *C12N 5/0657* (2013.01); *C12N 2506/02* (2013.01); *C12N 2501/155* (2013.01); *C12N 2501/16* (2013.01); *C12N 2501/727* (2013.01); *C12N 2506/45* (2013.01)

(58) Field of Classification Search
CPC .......................... C12N 5/0606; C12N 2506/00
See application file for complete search history.

(56) References Cited

U.S. PATENT DOCUMENTS

| | | |
|---|---|---|
| 7,452,718 B2 | 11/2008 | Gold |
| 2003/0022367 A1 | 1/2003 | Xu |
| 2003/0232431 A1 | 12/2003 | Law |
| 2005/0037489 A1 | 2/2005 | Gepstein et al. |
| 2007/0087437 A1 | 4/2007 | Hu |
| 2009/0169521 A1 | 7/2009 | Levenberg et al. |

FOREIGN PATENT DOCUMENTS

| | | |
|---|---|---|
| DE | 19843234 A1 | 3/2000 |
| WO | 2007/149926 A1 | 12/2007 |

OTHER PUBLICATIONS

Yu et al. Toxicol Sciences 2005;378-93.*
Horton et al. Regen Med Sep. 2009;4:721-32.*
Ng et al. Develop 2005;132:873-884.*
Wikipedia: Embryoid Body, 2012.*
Eastham et al. Cancer Res 2007;67;11254-62.*
Wikipedia contributors, Gonocyte, Wikipedia, 2013.*
Wikipedia contributors, Stem Cell, Wikipedia, 2013.*
Nelson, T.J. et al, "Repair of acute myocardial infarction by human stemness factors induced pluripotent stem cells," Circulation, Jul. 20, 2009, vol. 120, pp. 408-416.
International search report PCT US2003/023174.
Maltsev, V.A. et al., "Embryonic stem cells differentiate in vitro into cardiomyocytes representing sinusnodal, atrial and ventricular cell types," 1993, Mechanisms of Development, vol. 44, pp. 41-50.
Vogel, G. "Wisconsin to distribute embryonic cell lines," Feb. 11, 2000. Science, vol. 287, No. 5455, pp. 948-949.
Burridge, P.W. et al, "Improved human embryonic stem cell embryoid body homogeneity and cardiomyocyte differentiation from a novel V-96 plate aggregation system highlights interline variability," 2007, Stem Cells, vol. 25, pp. 929-938.
Bauwens, C.L. et al, "Control of human embryonic stem cell colony and aggregate size heterogeneity influences differentiation trajectories," 2008, Stem Cells, vol. 26, pp. 2300-2310.
Thomson, J. A. et al, "Embryonic stem cell lines derived from human blastocysts," Nov. 6, 1998,Science, vol. 282, pp. 1145-1147.
Kehat, I. et al, "Human embryonic stem cells can differentiate into myocytes with structural and functional properties of cardiomyocytes," 2001, Journal of Clinical investigation, vol. 108, No. 3 pp. 407-414.
He, Jia-Qiang et al, "Human embryonic stem cells develop into multiple types of cardiac myocytes: action potential characterization," 2003, Circulation Research, vol. 93, pp. 32-39.
Maltsev, V.A. et al, "Cardiomyocytes differentiated in vitro from embryonic, stem cells developmentally express cardiac-specific genes and ionic currents," Circulation Research, 1994, vol. 75, No. 2, pp. 233-244.
Puceat et al., Protocols for cardiac differentiation of embryonic stem cells; 45:168-171 (2008).
Zhang et al., Circulation; 120:S1123-S1124 (2009).
International Search Report and Written Opinion, PCT/US2010/056653; dated May 25, 2011.
Solnica-Krezel "Conserved Patterns of Cell Movements during Vertebrate Gastrulation" Current Biology, Mar. 29, 2005, pp. R213-R228, vol. 15.

* cited by examiner

*Primary Examiner* — Janice Li
(74) *Attorney, Agent, or Firm* — Quarles & Brady LLP

(57) ABSTRACT

Methods for culturing the pluripotent stem cells to undergo epithelial-to-mesenchymal transition and for generating high-yield, high-purity cardiomyocyte cultures from pluripotent stem cells are described. Pluripotent stem cells are cultured on a support with an overlaid matrix and, optionally, exposed to one or more factors to induce epithelial-to-mesenchymal transition and cardiogenesis.

23 Claims, 10 Drawing Sheets

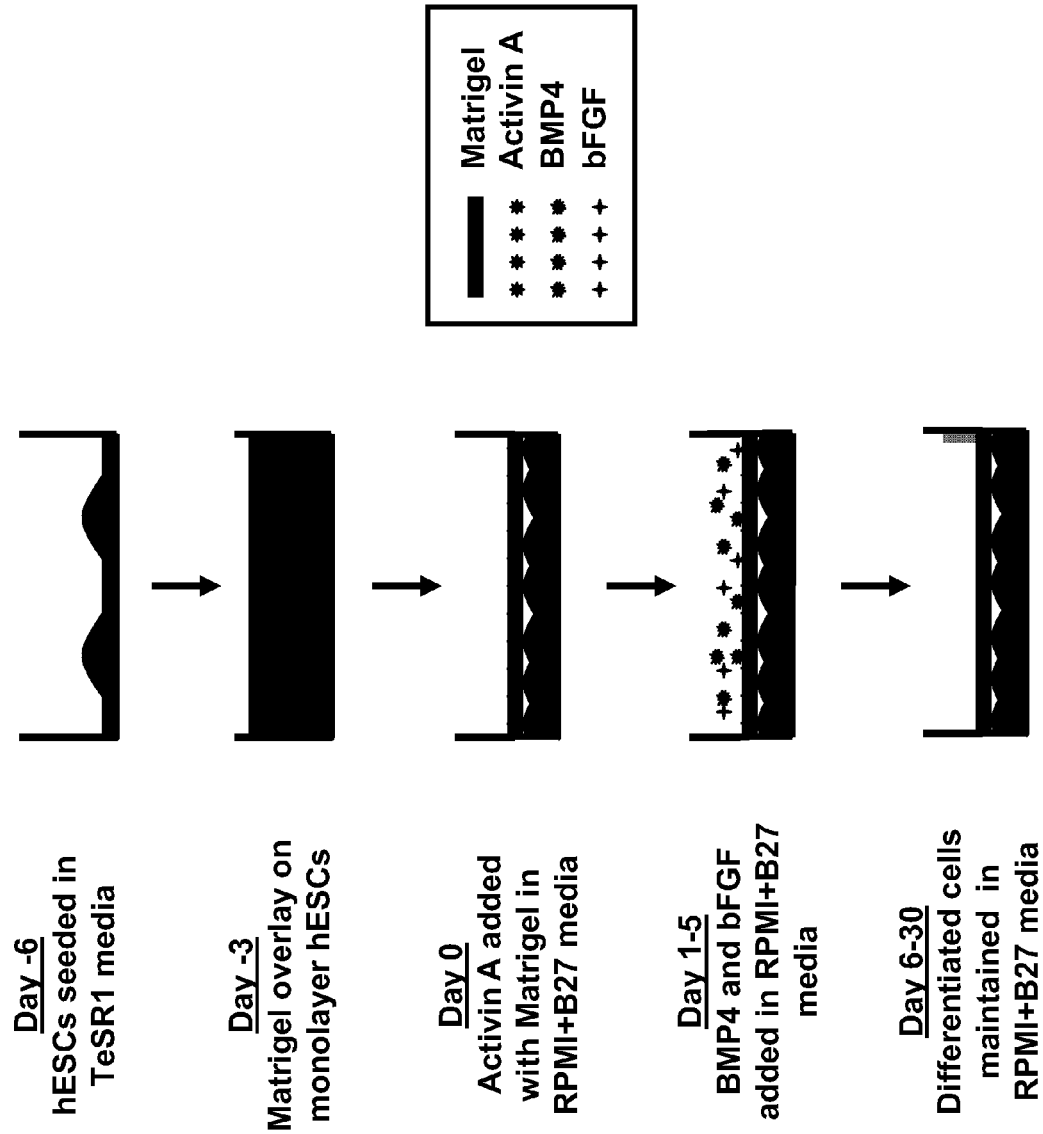

MATRIX OVERLAY

CARDIAC DIFFERENTIATION OF HUMAN PLURIPOTENT STEM CELLS UNDER DEFINED CONDITIONS USING MATRIX OVERLAY METHODS

CROSS-REFERENCE TO RELATED APPLICATIONS

This application claims the benefit of U.S. Provisional Patent Application No. 61/261,054, filed Nov. 13, 2009, incorporated herein by reference as if set forth in its entirety.

STATEMENT REGARDING FEDERALLY SPONSORED RESEARCH OR DEVELOPMENT

This invention was made with government support under R01 EB007534 and EFRI-0735903 awarded by The National Institute of Health and the National Science Foundation, respectively. The government has certain rights in the invention.

BACKGROUND

Generating cardiovascular cells from pluripotent stem cells holds great promise for cardiovascular research and therapy. However, pluripotent stem cell differentiation into cardiac cells is inefficient and results in heterogeneous cultures, limiting the usefulness of this approach. Pluripotent stem cells, such as human embryonic stem (hES) cells and induced pluripotent stem (iPS) cells, can perpetually proliferate and differentiate into derivatives of all three embryonic germ layers (Thomson et al., Science 282:1145 (1998); Odorico et al., Stem Cells 19:193 (2001); Yu et al., Science 318 (5858):1917 (2007)). Differentiation of pluripotent stem cell cultures can occur spontaneously, which results in a seemingly random variety of cells (Watt and Hogan, Science 287: 1427 (2000)). The earliest methods of pluripotent stem cell differentiation included allowing stem cell aggregates to spontaneously differentiate and form embryoid bodies (EBs) which contain derivatives of the three primary germ layers including in some cases cardiomyocytes.

Generating cardiomyocytes from pluripotent stem cells through EB formation is inefficient, however, as only few percent of the developing cells become cardiomyocytes. Efficient, reproducible methods for differentiating human pluripotent stem cells into cardiovascular cell lineage remain to be elucidated.

More recently, researchers attempted to improve efficiency by differentiating hES cells into cardiomyocytes without EB formation by sequentially applying growth factors or small molecules to mimic cardiac development. Soluble factors important for embryonic cardiac development include Activin A, BMP4, nodal, Wnt agonists and antagonists, bFGF and other molecules (Conlon et al., Development 120(7): 1919 (1994); Lough et al., Dev. Biol. 178(1):198 (1996); Mima et al., PNAS 92(2):467 (1995); Zaffran and Frasch, Circ. Res. 91 (6), 457 (2002)). Various combinations of these factors have been tested in cardiac differentiation protocols. Treatment with Activin A and BMP4 promoted cardiogenesis of H7 ES cells grown as monolayers (Laflamme et al., Nat. Biotechnol. 25 (9):1015 (2007)). Other protocols employed EB-based differentiation and enhanced cardiogenesis by using various combinations of BMP4, Activin A, bFGF, VEGF, and dickkopf homolog 1 (DKK1) (Yang et al., Nature 453 (7194):524 (2008)). The latter protocols were performed using H1 and HES2 human ES cell lines and have not been demonstrated to work with other ES cell lines or iPS cell lines.

iPS cells are generated by reprogramming somatic cells or differentiated progenitor cells to a state of pluripotency. Apart from their somatic cell origin, iPS cells share many characteristics of embryonic stem cells, such as the ability to grow perpetually and to differentiate into cells of all three germ layers. Like ES cells, iPS cells express pluripotency markers, such as OCT-4, SSEA-3, SSEA-4, TRA-1-60, TRA-1-81, and Nanog. iPS cells have been generated using retroviral vectors that randomly insert exogenous DNA into the target cell genome. More recently, vector- and transgene-free iPS cells have been generated by using non-integrating vectors. Using non-integrating vectors avoids the risk of aberrant cellular gene expression and neoplastic growth (Okita et al. Nature 448:313 (2007)). Loss of the reprogramming vector also avoids perpetual expression of transgenes that can induce programmed cell death (apoptosis) (Askew et al., Oncogene 6:1915 (1991), Evan et al., Cell 69:119 (1992)) and interfere with subsequent differentiation of iPS cells.

More recently, methods were devised for reprogramming somatic cells using oriP/Epstein-Barr nuclear antigen-1 (EBNA1)-based episomal vectors that do not integrate into the genome and are lost from the cells after reprogramming (Yu et al., Science 324(5928):797 (2009)). iPS cells generated by this method are vector- and transgene-free and, as such, are well suited for clinical application. However, the ability of these vector-free iPS cells to form EBs or to differentiate into various cells types, such as cardiomyocytes, useful for clinical application has been unknown.

During embryonic development as the primitive streak forms, a migratory population of the epiblast cells undergoes an epithelial-to-mesenchymal transition (EMT) during gastrulation to generate mesodermal cells. This marks the first step in differentiation to mesoderm and, ultimately, to cells of the mesodermal lineage, such as cardiomyocytes.

EMT is an important biological phenomena implicated in multiple steps of development and other healthy and diseased physiological processes, such as cancer metastasis. For example, breast cancer cells initially are characterized by an epithelial phenotype but assume a mesenchymal phenotype during tumor metastasis. This transformation enables the cells to dissociate from their tissue of origin, enter the circulation, and establish metastases in remote tissues sites.

Prior to the inventors' work, no efficient cardiac differentiation protocol demonstrated broad applicability across multiple ES and iPS cell lines. Also, available differentiation protocols relied on the application of soluble growth factors to direct differentiation and failed to consider the role of extracellular matrix in promoting the first differentiation steps of ES and iPS cells necessary to generate mesoderm and subsequent cardiomyocytes.

BRIEF SUMMARY

In a first aspect, the invention is summarized in that a method for culturing pluripotent stem cells includes the step of culturing the cells in feeder-free, defined medium that upon addition of an overlay of matrix, such as MATRIGEL®, can efficiently induce epithelial-to-mesenchymal transition. The disclosed method is highly reproducible because the culture medium can be completely defined. The invention is effective for use with pluripotent stem cells, including but not limited to primate, including human, ES and iPS cells.

In some embodiments of the first aspect, the method includes the step of culturing the cells to efficiently direct the differentiation of the cells to cardiomyocytes. Cardiogenesis can be facilitated by contacting the cells with one or more factors. When compared to cell populations produced by existing differentiation protocols, the methods of the invention produce cell populations characterized by high cardiomyocyte yield and superior purity, e.g., 1 input stem cell can generate up to 10 cardiomyocytes with 30-90% of the cells being cTnT-positive cardiomyocytes. Advantageously, the method does not require the formation of embryoid bodies.

In some embodiments of the first aspect, efficient cardiac differentiation of human pluripotent stem cells to cardiomyocytes is effected by simultaneous or sequential application of growth factors, such as Activin A, BMP4, and bFGF to pluripotent stem cells grown between layers of matrix that supports cell growth in defined media.

In some embodiments of the first aspect, efficient cardiac differentiation of human pluripotent stem cells to cardiomyocytes is effected by a one-day exposure to Activin A following the matrix overlay.

In some embodiments of the first aspect, the medium is completely defined and, in some cases, is substantially free of insulin. As used herein, "substantially free" means a de minimus or reduced amount of insulin, such that the insulin concentrations in the medium is too low to produce a biological response to insulin in the pluripotent stem cells. "Substantially free" also means that the medium in some cases does not contain any detectable amount of insulin.

In some embodiments of the first aspect, the cells are contacted with an agent to determine if it modulates epithelial-to-mesenchymal transition. As used herein, "modulate" means that the agent positively or negatively affects the process of EMT by either increasing, enhancing, accelerating or by decreasing, delaying, inhibiting the process. One Example of such agent is Activin A.

In a second aspect, the invention is summarized as a culture composition that includes a support, pluripotent stem cells, and a matrix layer. The support and the matrix layer contact the pluripotent stem cells, at least some which are organized in the culture in foci that comprise N-cadherin-positive cells. The foci can be about 100-200 µm in diameter.

In a third aspect, the invention is summarized in that a method for forming EBs from vector-free iPS cells includes culturing substantially undifferentiated vector-free iPS cells under differentiating culture conditions until EBs are formed. Advantageously, the cells of the EB and any cells subsequently derived therefrom are likewise free of the vector used for reprogramming of somatic or differentiated precursor cells to create the underlying iPS cells.

In a fourth aspect, the invention is summarized in that a method for generating vector-free cardiomyocytes includes culturing substantially undifferentiated vector-free iPS cells under differentiating culture conditions until the culture contains cardiomyocytes.

BRIEF DESCRIPTION OF THE DRAWINGS

FIG. 1 illustrates a schematic of an example culturing method employing an overlay of a matrix that supports cell growth and promotes the epithelial-to-mesenchymal transition followed by subsequent addition of growth factors to direct pluripotent stem cell differentiation into cardiomyocytes under defined conditions.

FIG. 2 illustrates a flow cytometric analysis for cardiac troponin T (cTnT) expression in cells differentiated from ES cells (H9) grown either in the presence (Matrix overlay, MO) or absence (control) of a MATRIGEL® overlay.

FIG. 3 illustrates a flow cytometric analysis for cTnT expression in ES cells (H1 and H9) and iPS cells (DF6-9-9T and DF19-9-11T) from either embryoid bodies (EB) or matrix overlay cultures (MS).

FIG. 6A depicts cells grown in the absence of a matrix overlay.

FIG. 8A illustrates percent purity of cTnT-positive cardiomyocytes after exposure with varying concentrations of Activin A in defined media (RPMI with B27 without insulin supplement) added with a MATRIGEL overlay to enhance growth factor delivery. FIG. 8B illustrates cardiomyocyte yield per input of iPS cells after exposure to various concentrations of Activin A. FIG. 8C illustrates purity of cTnT-positive cardiomyocytes after exposure with varying concentrations of BMP4 and bFGF at day 1-5. FIG. 8D illustrates cardiomyocyte yield per iPS cell input after exposure to various concentrations of BMP4 and bFGF during day 1-5.

DETAILED DESCRIPTION OF PREFERRED EMBODIMENTS

Figure 2B:
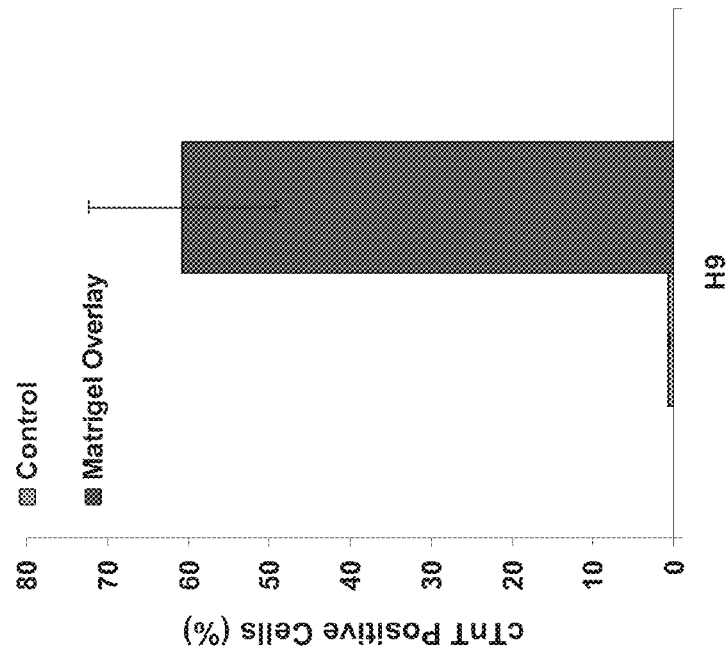
FIG. 2B depicts the average percentage of cTNT-positive cells from three independent experiments for each condition.

Reproducible and efficient methods for differentiating human pluripotent stem cells to cardiomyocytes in vitro has been highly desired. The present invention provides methods for culturing pluripotent stem cells under defined conditions to obtain a cell population highly enriched in cardiomyocytes. The methods involve plating pluripotent stem cells onto a support, adding a matrix overlay, and culturing the pluripotent stem cells to form a differentiated cell population that comprises cardiomyocytes. The methods can include the step of inducing differentiation by adding certain factors to the pluripotent stem cell culture. Examples of such factors include Activin A, bone morphogenetic protein 4 (BMP4), and basic fibroblast growth factor (bFGF) but other factors that promote cardiogenesis can be used in the described methods. The factors can be added to the cells simultaneously or sequentially. In one embodiment, the factors Activin A, BMP4, and bFGF are added at a concentration of 100 ng/ml, 10 ng/ml, and 5-10 ng/ml, respectively.

In some embodiments, one or more of the factors can be mixed with the matrix. The matrix can be any matrix that supports cell growth, such as MATRIGEL®. Similarly, the support can be any support that sustains cell growth, such as a matrix or chemically defined surface. As used herein, "matrix overlay method" refers to cells grown on a support with a matrix overlaying the cells. Specifically contemplated are embodiments that include multiple matrices overlaying multiple cells grown on supports. Such embodiments can be arranged, for example, in a stacked configuration so that a matrix overlay for a first population of cells functions as support for a second cell population. The matrix overlay can also result in at least some of the cells being partially or fully surrounded by the matrix.

In some embodiments, the matrix overlay method as described herein results in differentiated cell populations that comprise 30-90% cTnT-positive cardiomyocytes. As used herein, "cardiomyocytes" refer to cardiac muscle cells at various stages of maturity. Cardiomyocytes can be characterized by the expression of one or more cardiac marker, such as NKX2.5, cTnT, alpha-myosin heavy chain, cardiac actin, phospholamban, myosin light chain 2a (MLC2a), and myosin light chain 2v (MLC2v). The methods advantageously produce approximately 4-11 cardiomyocytes per pluripotent stem cell used in the described methods.

The skilled artisan will appreciate the advantageous efficiency of using defined media conditions, i.e., defined media that do not contain serum. As used herein, a "defined medium" refers to a formulation of biochemically-defined constituents that can include constituents of known chemical composition. Pluripotent stem cells used in the method can be cultured in any medium that supports pluripotent stem cell growth, including but not limited to a defined medium, such as TESR™ (StemCell Technologies, Inc.; Vancouver, Canada), MTESR™ (StemCell Technologies, Inc.) and STEMLINE® serum-free medium (Sigma; St. Louis, Mo.), or a conditioned medium such as mouse embryonic fibroblast (MEF)-conditioned medium. As used herein, "conditioned medium" refers to a growth medium that contains soluble factors from cells cultured in the medium. Alternatively, cells can be maintained on MEFs in culture medium.

Similarly, the pluripotent stem cell-derived cardiomyocytes produced by the described methods can be cultured in any medium that supports cell growth, including but not limited to a defined medium, such as RPMI 1640 (Gibco). The medium can be supplemented with nutritional supplements that support cardiomyocyte growth, such as B27 supplement (Gibco).

As used herein, a "vector-free iPS cell" refers to a pluripotent stem cell obtained by reprogramming a somatic or differentiated precursor cell using a non-integrating episomal vector. Because the vector is lost from the cell after reprogramming, the iPS cell is vector-free. Examples of such episomal vectors are oriP/Epstein-Barr nuclear antigen-1 (EBNA1)-based episomal vectors, as described in Yu et al., Science 324(5928):797-801 (2009), incorporated herein by reference as if set forth in its entirety.

Vector-free iPS cells can be differentiated by co-culture with cells of particular lineages or by adding one or more factors to the culture. Alternatively, the cells can be chemically or mechanically detached from their substrate to induce embryoid body formation.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Example 1

EB Formation and Cardiogenesis by Vector-Free iPS Cells

Four human iPS clones (iPS-DF6-9-9T, iPS-DF6-9-12T, iPS-DF19-9-7T, and iPS-DF19-9-11T) were obtained by reprogramming foreskin fibroblasts using oriP/Epstein-Barr nuclear antigen-1 (EBNA1)-based episomal vectors, as described in Yu et al., (2009). The cell lines were maintained either on mouse embryonic fibroblasts for embryoid body (EB) formation or in feeder-free TESR™ medium for directed differentiation.

Figure 5:
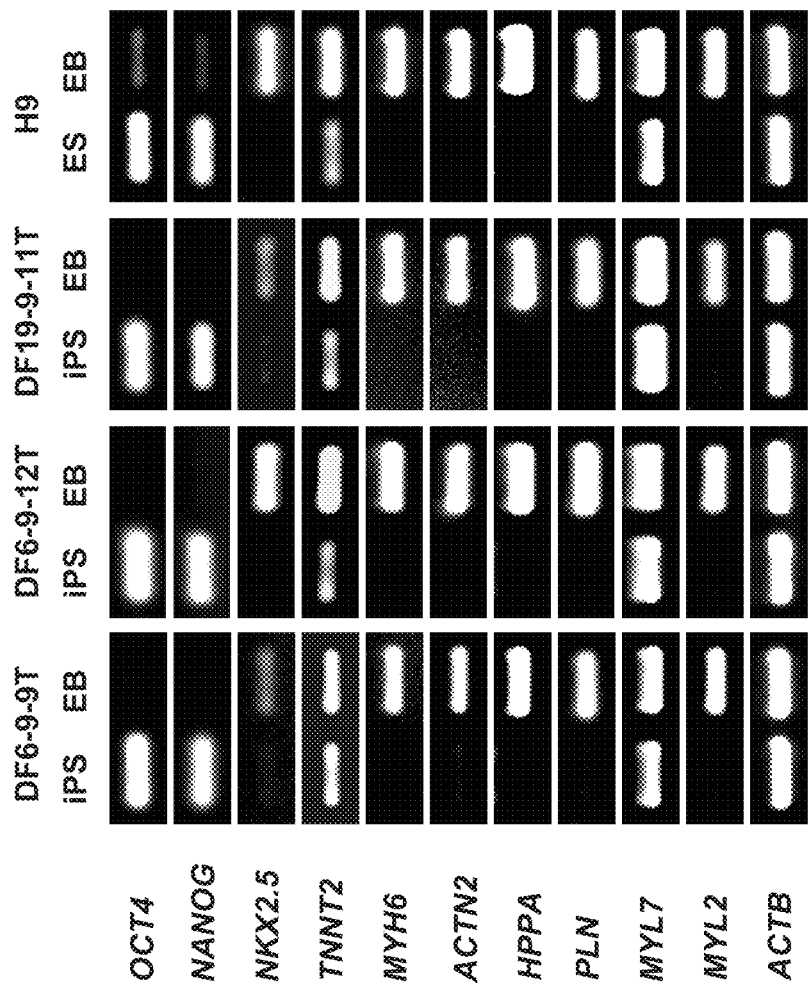
FIG. 5 illustrates reverse transcription polymerase chain reaction analysis of OCT4, NANOG, NKX2-5, TNNT2, MYH6, ACTN2, HPPA, PLN, MYL7 and MYL2 expression in undifferentiated iPS and ES cells and d60 EBs from three vector-free iPS cell lines, DF6-9-9T, DF6-9-12T and DF19-9-11T, compared to H9 ES cell line.

Contracting outgrowths formed on EBs from vector-free iPS cells. To form EBs, iPS cell colonies were detached from 6-well plates using 1 mg/ml dispase solution. EBs were cultured in suspension for 4 days in cardiac differentiation medium containing 20% FBS. The cells were subsequently plated onto 6-well plates and differentiated for up to 60 days. The percentage of contracting EBs was measured at day 6, 8, 10, 15, 20, 30, and 60. EBs from the four iPS clones generated contracting outgrowths (iPS-DF6-9-9T: 2.8±0.7%; iPS-DF6-9-12T: 8.2±0.8%; iPS-DF19-9-7T: 0.1±0.07%; iPS-DF19-9-11T: 2.5±0.2%, expressed as percent of whole EB that contracts). Consistently, cells from the iPS-derived EBs were characterized by increased cardiac gene expression and decreased pluripotency gene expression (FIG. 5). Total RNA from undifferentiated iPS cells as well as microdissected contracting areas from d60 EBs formed from iPS cells was isolated using TRIZOL® Reagent (Invitrogen, Carlsbad, Calif.) and subjected to reverse transcription polymerase chain reaction (RT-PCR). Over the course of differentiation from pluripotent stem cells to pluripotent stem cell-derived cardiomyocytes, the cells upregulated the cardiac genes NKX2-5, TNNT2, MYH6, ACTN2, HPPA, PLN, MYL2 and MYL7 and concomitantly downregulated the pluripotency genes OCT4 and NANOG (FIG. 5).

Electrophysiological analysis demonstrated that EBs formed from vector-free iPS contained cardiomyocytes exhibiting typical cardiac-type action potentials. Single spontaneous contracting EB outgrowths were microdissected and plated onto glass coverslips (n=34 cells from 5 EB) 1-10 days prior to recording. Cardiomyocyte activity was assessed on days 56-70 post-EB formation using sharp microelectrodes (50-100 MΩ; 3M KCl) in a 37° C. bath continuously perfused with Tyrodes solution (in mM: 140 NaCl, 5.4 KCl, 1.8 $CaCl_2$, 1 $MgCl_2$, 10 Hepes, 10 glucose, pH 7.4 NaOH). Junction potentials and capacitance were nulled and data acquired at 10 kHz using an AxoClamp2A amplifier and pClamp 9.2 software (Axon Instruments, Sunnyvale, Calif.). For analysis, data were filtered off-line using a low pass Gaussian filter with a cut-off frequency of 2 kHz. Sharp microelectrode recordings revealed spontaneous cardiac action potentials.

Likewise, directed differentiation of iPS cells without matrix overlay using sequential treatment with Activin A (100 ng/ml) and BMP4 (10 ng/ml) resulted in the formation of contracting cardiomyocytes. Directed differentiation was performed using sequential treatment of Activin A (100 ng/ml) for 1 day, followed by BMP4 (10 ng/ml) and bFGF (5 ng/ml) in defined medium of RPMI plus B27 complete supplement. Taken together, the results demonstrate that vector-free iPS cells are capable of undergoing cardiogenesis using both EB methods and directed differentiation.

Example 2

Matrix Overlay-Directed Cardiogenesis of ES Cells and Vector-Free iPS Cells

The four human iPS cell lines iPS-DF6-9-9T, iPS-DF6-9-12T, iPS-DF19-9-7T, and iPS-DF19-9-11T were obtained as described in Example 1. iPS clones and the hES cell line H9 were maintained either on mouse embryonic fibroblasts for EB formation or in feeder-free TESR™ medium for directed differentiation, as described in Example 1.

Reference is made to FIG. 1 illustrating the matrix overlay method. hES cells and iPS cells maintained on mouse embryonic fibroblasts (MEFs) were seeded onto 6-well cell culture plates coated with growth factor-reduced MATRIGEL® (Becton-Dickinson Bioscience, Medford, Mass.) at a concentration of 0.5 mg/6-well plate. Cells were cultured in TESR™ medium (The WiCell Research Institute, Madison, Wis.) for 5 days and were singularized using Versene (Invitrogen) (Day-6). Cells were seeded at a density of 100,000 cells/cm$^2$ on 6-well plates. When cultures became confluent after 3-4 days, 0.5-1.0 mg MATRIGEL® was overlaid onto the cells for each 6-well plate at the medium change (Day-3). After 2-3 days in MTESR™ medium, 100 ng/ml Activin A (R&D) was added with 0.5 mg/plate MATRIGEL® mixed with RPMI 1640 plus B27 complete supplement (Day 0). At day 1, cells were treated with BMP4 (10 ng/ml) and bFGF (5-10 ng/ml) for 3-4 days without medium change (Day 1-5). Cells were maintained for up to 30 days in RPMI 1640 plus B27 complete supplement with medium changes every 3 days (Day 6-30).

Figure 2A:
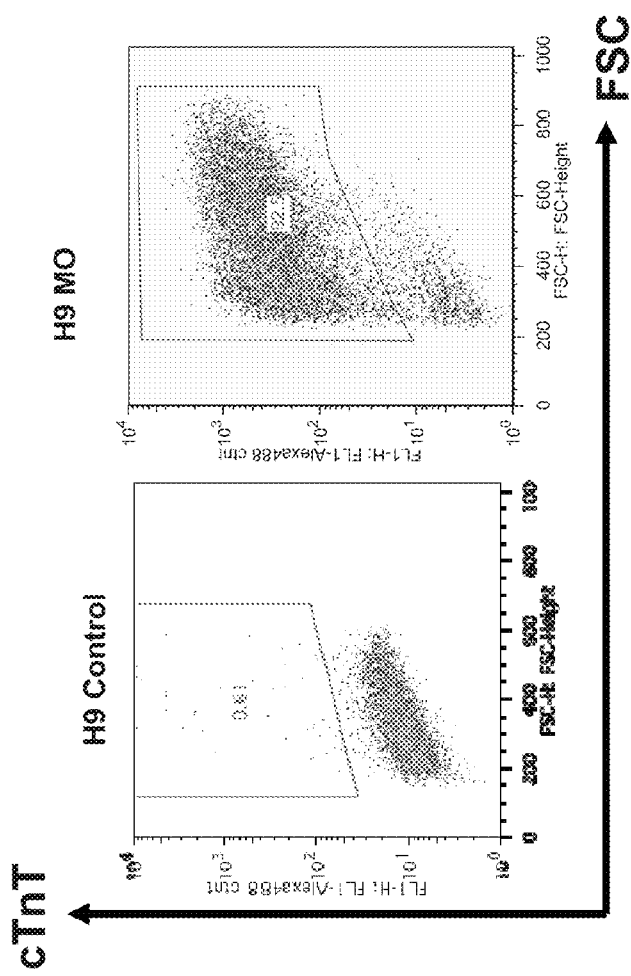
FIG. 2A depicts a dot plot of the flow cytometry analysis.

Human ES or iPS cells were exposed to sequential application of Activin A (100 ng/ml), BMP4 (10 ng/ml), and bFGF (5 ng/ml) either with MATRIGEL® overlay (MO) or without MATRIGEL® overlay (control). Without the MATRIGEL® overlay, only few cells differentiated into cardiomyocytes (FIGS. 2A and B, control). However, the matrix overlay method produced a cell population containing over ninety percent cardiomyocytes (FIGS. 2A and B, MO, matrix overlay).

Figure 3A:
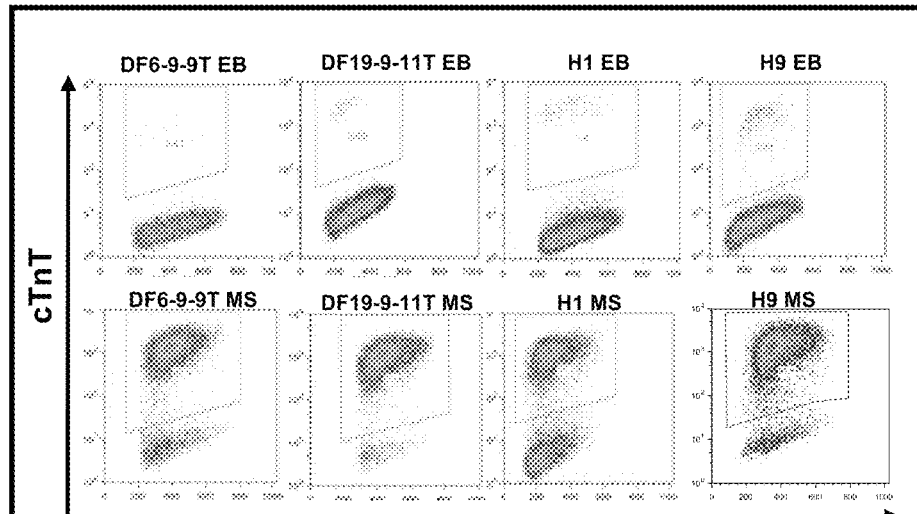
FIG. 3A depicts a dot plot of the flow cytometry analysis.
Figure 3B:
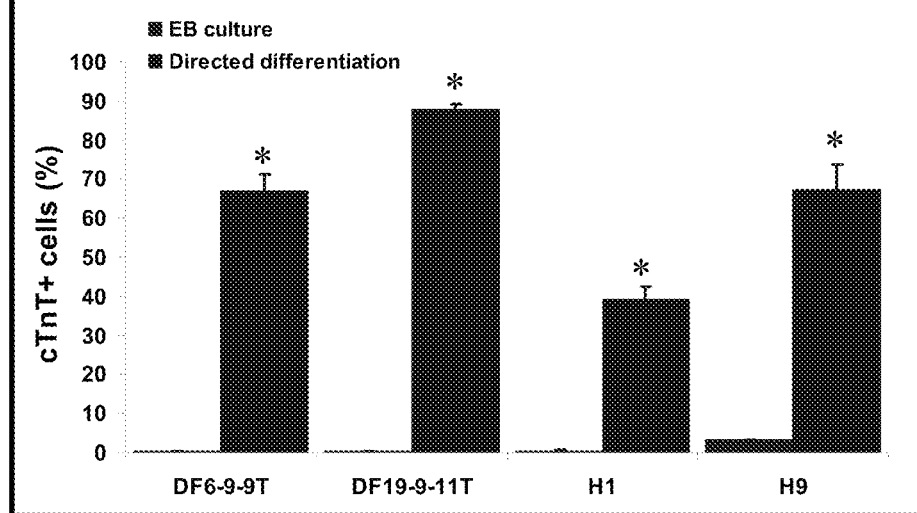
FIG. 3B depicts the average percentage of cTNT-positive cells from three independent experiments for each condition. The asterisks indicate statistical significance.

The matrix overlay method produced cell populations that were enriched in cardiomyocytes and had approximately 80-290 fold greater purity than the EB method. Also, the matrix overlay method resulted in enhanced yields of ES cell and iPS cell cardiomyocytes. For H9 ES cells, the matrix overlay method produced, on average, 4 cardiomyocytes for each starting ES cell, for vector-free iPS cell line DF19-9-11, the matrix overlay method produced, on average, 11 cardiomyocytes for each starting iPS cell. iPS cells and hES cells from day 30 EB cultures or matrix overlay cultures were trypsinized and counted. Cells were fixed in 1% paraformaldehyde and permeabilized in 90% ice-cold methanol. Cells were labeled with an antibody recognizing cardiac troponin T, a cardiac-specific myofilament protein, and analyzed using a FACSCaliber flow cytometer (Becton Dickinson). The matrix overlay method produced dramatically more cardiomyocytes than the EB method (FIG. 3A-B).

Figure 4:
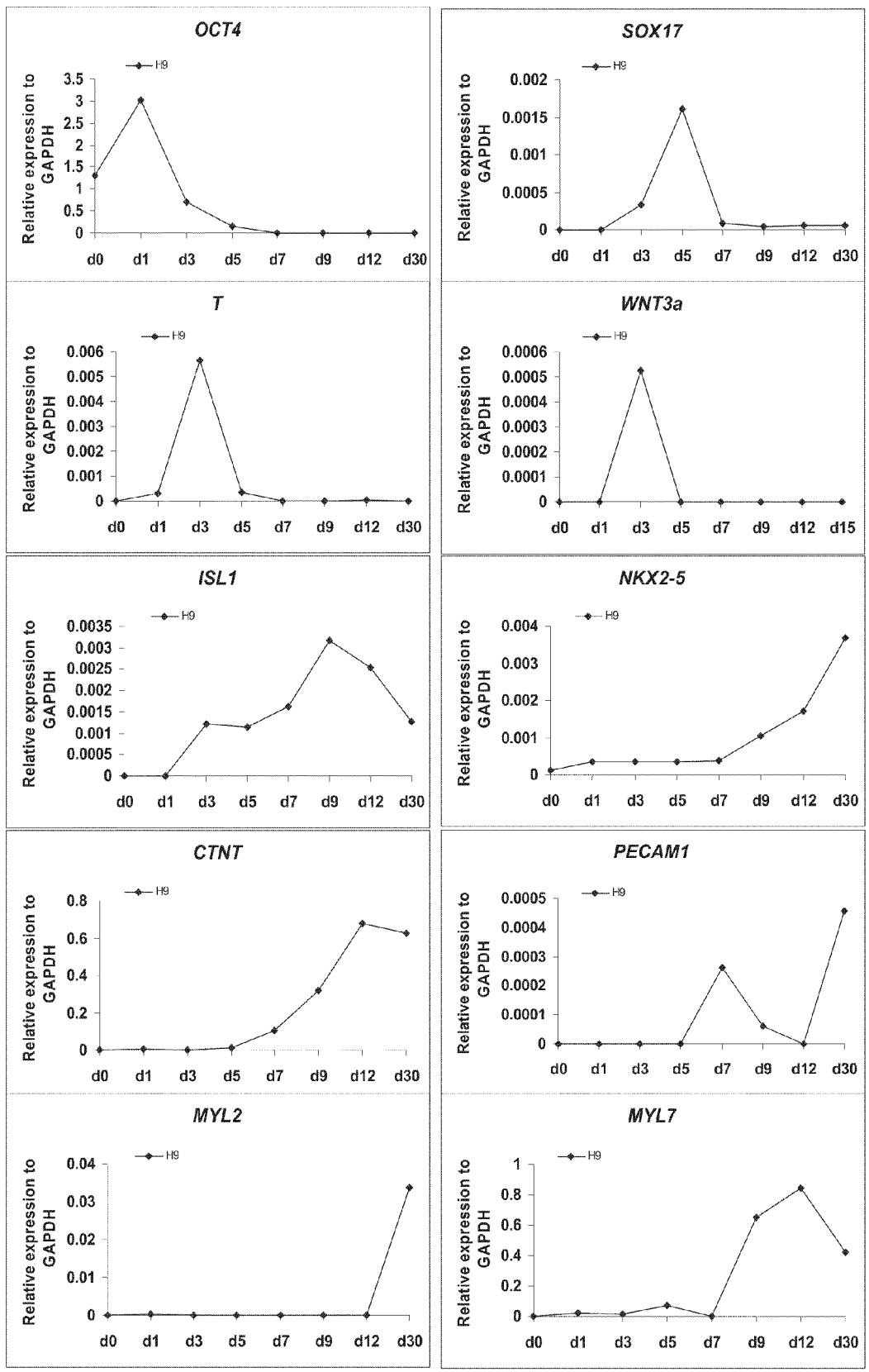
FIG. 4 illustrates a time course of gene expression in matrix overlay cultures. QPCR analysis of expression of OCT4, SOX17, T, WNT3A, ISL1, NKX2-5, PECAM1, TNNT2, MYL7, and MYL2 relative to GAPDH is shown.

During the course of differentiation from undifferentiated cells to iPS and ES cell-derived cardiomyocytes, cardiac gene expression was strongly upregulated while pluripotency gene expression was downregulated. Total RNA from undifferentiated iPS and ES cells as well as microdissected contracting areas from day 60 EBs was isolated and subjected to quantitative RT-PCR as described in Example 1. Over the course of differentiation from pluripotent stem cells to pluripotent stem cell-derived cardiomyocytes, the cells upregulated the cardiac genes NKX2-5, TNNT2, MYH6, ACTN2, HPPA, PLN, MYL2 and MYL7 and concomitantly downregulated the pluripotency genes OCT4 and NANOG (FIG. 4).

iPS and ES cell-derived cardiomyocytes produced by the matrix overlay method showed organized sarcomere formation and produced large networks of contracting cardiomyocytes. iPS and ES cells were seeded onto coverslips. After 15 days of differentiation, the cells were fixed and immunolabeled with an anti-cTnT antibody (Thermo Scientific, Waltham, Mass.). Also, cells from directed differentiation matrix overlay cultures at day 30 were trypsinized and replated on coverslips and immunolabeled with antibodies specific to cTnT, α-actinin, MLC2a and MLC2v. Single cardiomyocytes isolated from EB cultures were also immunolabeled with the antibodies to cTnT, α-actinin, MLC2a and MLC2v using the same method. The immunofluorescence was detected using epifluorescence microscopy. The iPS and ES cell-derived cardiomyocyte cultures from both EBs and matrix overlay cultures formed organized sarcomeres, including an A band of the sarcomere between the α-actinin-positive Z-lines.

Electrophysiological analysis confirmed that the matrix overlay method generated cardiomyocytes, based on the presence of typical cardiac action potentials. After 30 days of differentiation, contracting cell aggregates were plated on a glass coverslip 1-7 days prior to recording. Transmembrane voltage was recorded using sharp microelectrodes and solutions as described in Example 1. These sharp microelectrode recordings revealed spontaneous cardiac action potentials typical of developing atrial, ventricular, and nodal cardiomyocytes.

Example 3

A Matrix Overlay Promotes Epithelial-to-Mesenchymal Transition

The four human iPS cell lines iPS-DF6-9-9T, iPS-DF6-9-12T, iPS-DF19-9-7T, and iPS-DF19-9-11T were obtained as described in Example 1. Human ES cell lines of H1, H9 were used as comparison. The iPS cells and ES cells were maintained on irradiated MEFs at a density of 19,500 cells/cm$^2$ in 6-well culture plates (Nunc, Rochester, N.Y.). Both iPS and ES cells were maintained in DMEM/F12 culture medium supplemented with 20% KnockOut serum replacer, 0.1 mmol/L non-essential amino acids, 1 mmol/L L-glutamine (all Invitrogen), and 0.1 mmol/L β-mercaptoethanol (Sigma). In addition, the iPS cell medium was supplemented with 100 ng/ml zebrafish basic fibroblast growth factor (zbFGF), purified from a bacterial expression system, and the hES cell medium was supplemented with 4 ng/ml human recombinant bFGF (Invitrogen).

Whole well staining for cardiac markers was performed by seeding the pluripotent stem cells on glass coverslips coated with 0.1% gelatin solution in 24-well plate, and differentiated cells at day 15 were fixed for immunolabeling. Single CMs were isolated from day 30 differentiated cells using 0.25% trypsin-EDTA (Invitrogen) plus 2% chick serum (Sigma) for 5-10 minutes at 37° C. Cells were washed and plated on glass coverslips coated with 0.1% gelatin solution in EB20 medium for 2 days to allow attachment. Cells were fixed in 4% paraformaldehyde for 15 minutes at room temperature, rinsed twice in PBS, and permeabilized in 0.2% Triton X-100

(Sigma) for 1 hour at room temperature. Samples were blocked with 5% non-fat dry milk (Bio-Rad) in 0.2% Triton X-100 solution and incubated for 2 hours at room temperature on a rotator followed by two washes with PBS. Primary antibodies, including mouse monoclonal anti-Oct-4 ($IgG_{2b}$, Santa Cruz, 1:100 dilution), rabbit polyclonal anti-Nanog (IgG, 1:100 dilution, Cosmo Bio Co Ltd), mouse monoclonal anti-SSEA4 (Abeam 1:100 dilution), monoclonal anti-α-actinin ($IgG_1$, Sigma, 1:500 dilution), mouse monoclonal anti-cTnT ($IgG_1$, Thermo Scientific, 1:200 dilution), mouse monoclonal anti-MLC2a ($IgG_{2b}$, Synaptic Systems, Germany, 1:400 dilution), rabbit polyclonal anti-MLC2v (IgG, ProteinTech Group, 1:200 dilution), rabbit polyclonal anti-laminin (Sigma L9393, 1:500 dilution), goat polyclonal anti-human E-cadherin antibody (R&D AF648), and rabbit polyclonal anti-N-cadherin antibody (Santa Cruz, sc-7939, 1:100 dilution), were added in 0.1% Triton X-100, 1% BSA in PBS solution and the samples were incubated overnight at 4° C. The samples were washed with 0.2% Tween 20 in PBS twice and 1×PBS twice. Secondary antibodies specific to the primary IgG isotype were diluted in the same solution as the primary antibodies and incubated at room temperature for one hour in the dark on a rotator. The samples were washed with 0.2% Tween 20 in PBS twice and 1×PBS twice. Nuclei were stained with DAPI (Invitrogen, 1:1000 dilution) for 5 minutes at room temperature followed by three washes with PBS. Glycoproteins on plasma membranes of both live cultured cells and fixed cells were labeled by incubation with Wheat germ agglutinin (WGA) fluorescein conjugates in media for 30 minutes at 37° C. for live cells, or in PBS buffer at room temperature for fixed cells, followed by two washes with PBS buffer. One drop of Gold Anti-fade reagent with DAPI (Invitrogen) was placed on each slide, and coverslips were applied. The slides were examined with an epifluorescence microscope (Leica DM IRB) or confocal microscope (Nikon, A1R) with the image analysis by the software of NIS-Elements BR3.0).

Cardiac differentiation via EB formation of human ES and iPS cells was performed essentially as described in Example 1. iPS cells and ES cells were passaged onto MEFs (~13,000 cells/cm$^2$) and cultured in maintenance media containing 80% DMEM/F12, 0.1 mmol/L non-essential amino acids, 1 mmol/L L-glutamine, 0.1 mmol/L β-mercaptoethanol, and 20% KnockOut SR (Gibco) for 4 days. Colonies were detached from 6-well culture plates by incubation with 1 mg/ml dispase (Gibco) solution at 37° C. for 8-15 minutes and placed in ultra-low attachment plates (Corning) in suspension culture for 4 days in EB20 medium containing 80% DMEM/F12, 0.1 mmol/L non-essential amino acids, 1 mmol/L L-glutamine, 0.1 mmol/L β-mercaptoethanol, and 20% fetal bovine serum (FBS, Gibco). EBs were plated onto 0.1% gelatin coated 6-well culture plates (Nunc) at a density of 50-100 EBs/well, and cultured in EB20 medium for a total of 10 days of EB formation. After 10 days of differentiation, the FBS concentration was reduced to 2%. The numbers of contracting EBs were measured at day 6, 8, 10, 15, 20, 30 and 60 of EB formation using a heated stage (37° C.) microscope.

Vector-free iPS cell lines DF6-9-9T and DF19-9-11T, lentivirally generated iPS cell line IMR90 C4 (Yu et al, Science) and BC-iPS, and ES cell lines of H1 and H9 were used for directed cardiac differentiation using the matrix overlay method. Three iPS cell lines derived from individuals with long QT syndrome 2 (LQTS2), three iPS cell lines derived from individuals with long QT syndrome 3 (LQTS3), and one cell line derived from an individual with Pompe's disease were also tested in the matrix overlay method.

Human iPS and ES cells maintained on MEFs were passaged on thin-coated MATRIGEL® (BD Biosciences) in 6-well plate (2.2 µg/cm$^2$) and cultured in MTESR™ 1 medium (WiCell) for 5-6 days to deplete the feeder cells. iPS and ES cells were washed with PBS, followed by addition of 1 ml Versene solution (Invitrogen) to each well and incubation at 37° C. for 3-5 minutes. Cells were harvested by adding an equal volume of MTESR™ 1 medium and transferred to a conical tube. Cells were counted using hemocytometer and centrifuged at 1,000 rpm for 5 minutes and resuspended in MTESR™ 1 medium supplemented with 5-10 µM ROCK inhibitor (Y-27632, CalBiochem). The cells were then plated at 100,000 cell/cm$^2$ onto MATRIGEL®-coated 6-well plates and cultured in MTESR™ 1 medium, which was changed daily. After 3-4 days of growth, the cells reached 80-90% confluency. At this time, 0.5-1 mg MATRIGEL® was dissolved in 15 ml cold MTESR™ 1 medium and 2.5 ml of this mixture was added to each well of a 6-well plate at the medium change to form a thin matrix overlay. The cells were cultured in MTESR™ 1 medium for another 2-3 days. When the cells reached confluency, directed differentiation was induced by adding Activin A (100 ng/ml, R&D Systems) and MATRIGEL® (0.5 mg MATRIGEL®/6-well plate) in cold RPMI 1640 basal medium (Invitrogen) plus B27 supplement without insulin (Invitrogen), designated day 0. After 24 hours, the medium was removed and fresh RPMI 1640 medium plus B27 supplement without insulin containing BMP4 (10 ng/ml, R&D Systems) and bFGF (5-10 ng/ml, Invitrogen) was added, and the cells were cultured for another 4 days without medium change. After day 5, cells were then maintained in the RPMI 1640 medium plus B-27 complete supplement (containing insulin) for a total of 30 days.

For electron microscopy imaging, iPS or ES cells grown in the presence or absence of a matrix overlay were fixed overnight at 4° C. in a 2.5% gluteraldehyde, 2% paraformaldehyde, 0.1 M phosphate buffer solution and then post-fixed with 1% osmium tetroxide. The fixed cell samples were then dehydrated with increasing concentrations of ethanol up to 100% and then kept in a 1:1 mixture of 100% EtOH and DURCUPAN™ embedding medium overnight. Samples were desiccated under vacuum for 3 hours, embedded in fresh DURCUPAN™ medium, and stored at 60° C. overnight for allow the embedding medium to polymerize. A 1 cm$^2$ sample of the culture dish was cut with a jeweler's saw for microtome processing. The samples were cut perpendicular to the culture surface at the interface of the dish and embedded cells into ultrathin 60 nm sections. The sections were placed on a copper grid and stained with uranyl acetate and lead citrate. The sections were visualized on a Phillips CM120 STEM and photographs were taken with an attached digital camera.

For RT-PCR and Quantitative RT-PCR of EBs, total RNA was isolated using Trizol Reagent (Invitrogen) from one well of a 6-well plate of undifferentiated iPS cells and ES cells and from 30-40 contracting areas microdissected from day 60 EBs from iPSCs or ESCs. Possible genomic DNA contaminations were removed by DNase I (Invitrogen) treatment for 15 minutes at room temperature. 500 ng of total RNA was used for Oligo(dT)$_{20}$-primed reverse transcription using SUPERSCRIPT™ III First-Strand Synthesis System (Invitrogen). RT-PCR was carried out using PLATINUM™ Taq DNA Polymerase (Invitrogen). PCR was conducted by denaturing at 94° C. for 30 seconds, annealing at 60° C. for 30 seconds, and extending at 72° C. for 1 minute, for 35 cycles, with 72° C. extension for 7 minutes at the conclusion of the reaction. ACTB (β-actin) was used as an endogenous control for RT-PCR. Cell samples from the timecourse of the matrix overlay cultures at day 0, 1, 2, 3, 4, 5, 7, 9, 12, 15, 20 and 30 were collected using trypsin to remove the cells from one well of 6-well plate. Total RNA was purified using QIAGEN RNE-ASY® Mini kit. Possible genomic DNA contamination was removed by DNase I (Invitrogen) treatment for 15 minutes at room temperature. Quantitative RT-PCR was performed using Taqman PCR Master Mix and Gene Expression Assay (Applied Biosystems) in triplicate for each sample and for each gene. 0.5 µl of cDNA from RT reaction was added as template for each Q-PCR reaction. Gene expression data were normalized to that of ACTB in Q-PCR.

Statistical significance was determined by Student's t-test (two-tail) for two groups or one-way ANOVA for multiple groups with post hoc testing using Tukey method using Microcal Origin, v7.5 software. P<0.05 was considered statistically significant. Data are presented as mean±standard error of the mean (SEM).

Figure 6A:
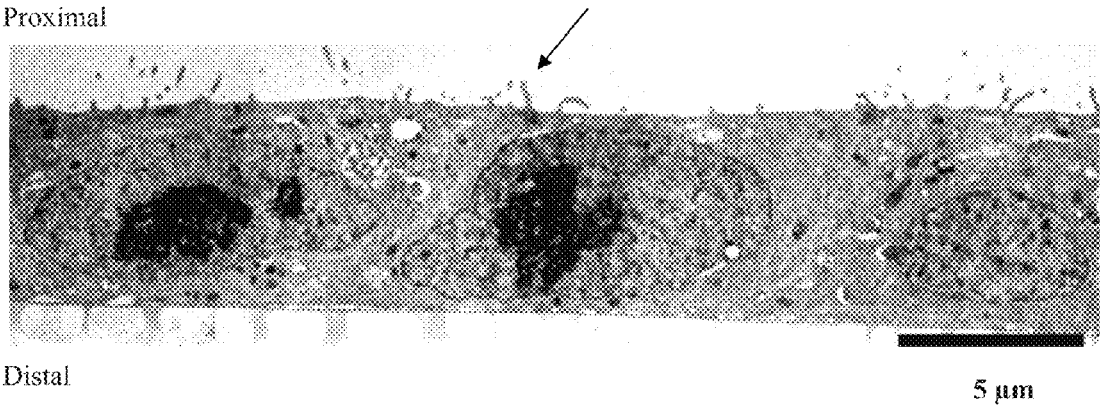
FIGS. 6A and B illustrate electron microscopy images.

ES cells and iPS cells cultured as a monolayer on a matrix exhibited a polarized epithelial cell-like phenotype similar to epiblast cells present in the early embryo. This epiblast phenotype was evident from microvilli on the apical cell surface (FIG. 6A, arrow) and robust expression of the adhesion junction protein E-cadherin and of epiblast genes Oct4, Nanog, and Sox2 on the cells' lateral surfaces. Epithelial polarization was also evident from the apical labeling of surface glycoproteins with wheat-germ agglutinin (WGA) with the basal surfaces growing on a layer of ECM containing laminin. To determine if ES and iPS cells grown as a monolayer could be induced to undergo EMT in vitro and, thereby, more efficiently differentiate into mesoderm cells and, ultimately, mesoderm lineages such as cardiomyocytes, a matrix overlay was applied essentially as described in Example 2.

Figure 6B:
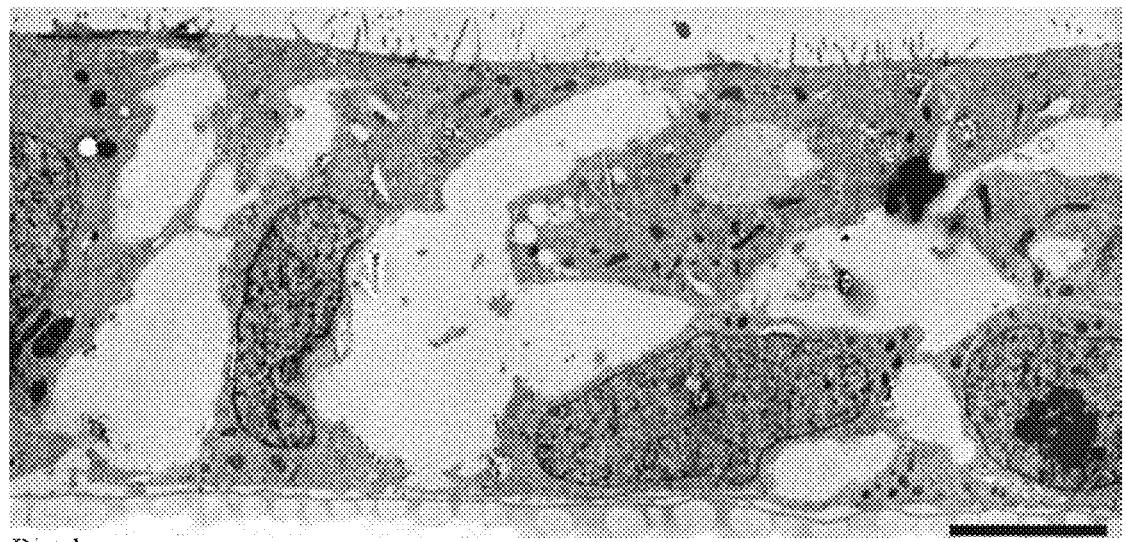
FIG. 6B depicts cells grown in the presence of a matrix overlay.

An overlay of extracellular matrix (growth factor-reduced MATRIGEL®) to the top of cultured human pluripotent stem cell monolayers induced rapid changes in cellular organization within 24 hours. Electron micrographs (FIG. 6B) and Z-scans of confocal images demonstrated that the cells formed isolated multilayered foci composed of mesenchymal-like cells underneath a layer of epithelial cells. These foci were slightly raised and typically had a diameter of approximately 100 to 200 µm. In some experiments, an average of 118 foci per 1.8 cm$^2$ were observed in cultures with the matrix overlay 24 hours after matrix overlay, whereas only 23 foci were present in control cultures without a matrix overlay. The overlaying matrix was quickly internalized by the epithelial cell layer as evident from matrix-sparse or matrix-free spaces between cells visible in electron micrographs at 24 hours and from confocal images of laminin immunolabeled cultures.

Figures 7A, 7B:
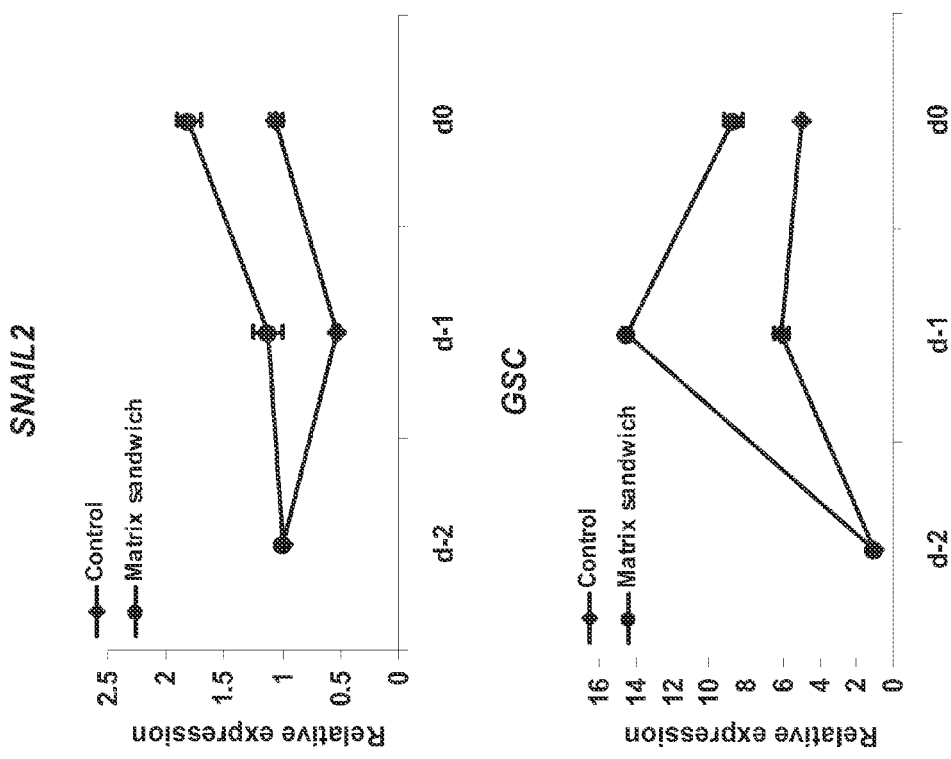
FIG. 7A-D illustrate Q-PCR measurement of the expression of SNAIL1 (FIG. 7A), SNAIL2 (FIG. 7B), VIM (FIG. 7C), and GSC (FIG. 7D) which are expressed in cells undergoing epithelial-to-mesenchymal transition.
Figures 7C, 7D:
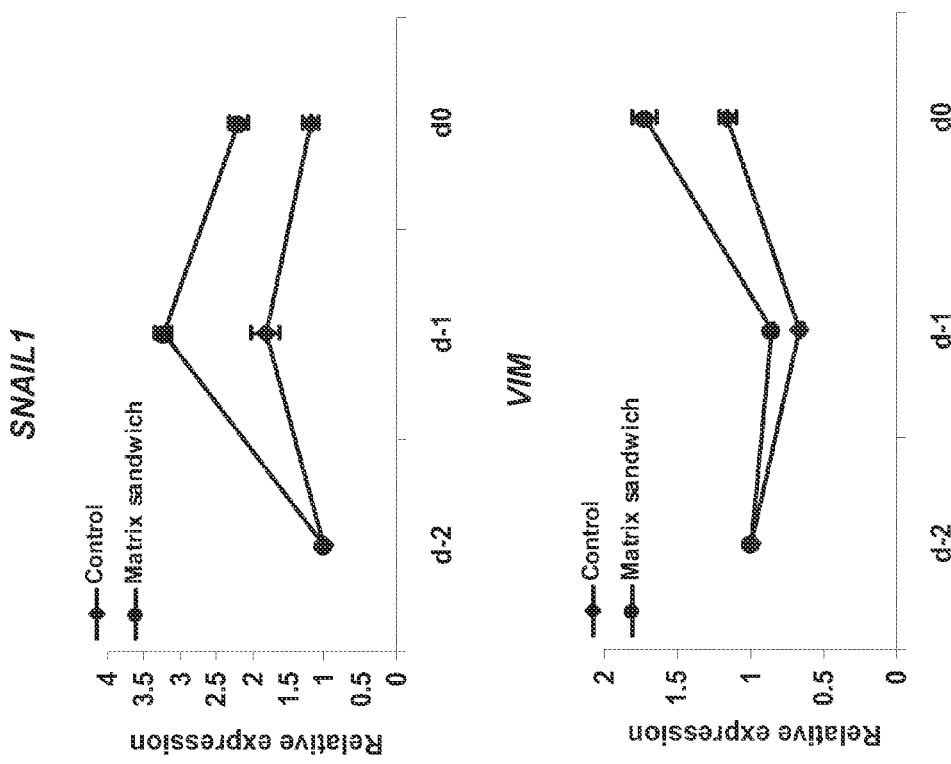

A hallmark change during EMT is the transition in cadherin expression from the epithelial E-cadherin to N-cadherin. In control cultures grown as monolayers without matrix overlay, E-cadherin was expressed throughout the monolayer with little or no expression of N-cadherin. In contrast, in cultures with a matrix overlay, surface-proximal cells, i.e., cells in the upper regions of the foci near the top culture surface, were linked by E-cadherin, while surface-distal cells, i.e., cells in lower regions of the foci near the culture dish bottom, lacked E-cadherin expression. Also, the matrix overlay cultures exhibited multiple foci of cells that expressed N-cadherin but not E-cadherin. These N-cadherin positive cells were present as clusters of surface-distal (lower layer) cells, as determined by confocal imaging. These surface distal cells exhibited a high nucleus-to-cytoplasm ratio, lacked regular cell-cell contacts and apico-basal polarity, which are characteristics of migratory mesodermal cells that develop during gastrulation. A commitment to the mesoderm lineage was also evident from the loss of Oct-4 expression by surface-distal N-cadherin positive mesenchymal cells, in contrast to the surface-proximal cells which retained robust Oct-4 expression. In addition, Q-PCR revealed that the matrix overlay increased expression of SNAIL1, SNAIL2, GSC, and other genes typically upregulated during EMT relative to control cultures (FIG. 7). Thus, application of apical matrix to pluripotent stem cells grown as monolayers induced EMT resulting in the formation of mesoderm-like cells.

Example 4

Efficient Matrix Overlay-Directed Cardiogenesis of ES Cells and Vector-Free iPS Cells To improve efficient differentiation of mesoderm-like cells generated in the matrix overlay cultures described in Examples 2 and 3 into cardiomyocytes, H9 human ES cells, lentiviral generated iPS cells (IMR-90-c4, foreskin-c1 (Yu. et al., Science 318(5858):1917 (2007)), and vector and transgene free iPS cells DF19-9-1 IT, DF6-9-9T (Yu, J. et al., Science 324(5928):797 (2009)) were differentiated to mesodermal cells, essentially as described in Example 3 and then the medium was changed to RMPI+B27, but no contracting cardiomyocytes were observed over the following 30 days suggesting the need to further direct the differentiation of the mesoderm-like cell population in order to generate cardiomyocytes.

Developmental studies in mouse embryos have suggested that the mesendoderm differentiation to mesoderm via EMT or alternatively to form definitive endoderm depends upon the duration and magnitude of Nodal/Activin signaling (Lowe et all, Development 128:1831-1843 (2001); Vincent et al., Genes Dev 17:1646-1662 (2003)).

Available endoderm differentiation protocols require continued presence of Activin A to favor definitive endoderm differentiation over mesodermal lineages (D'Amour, et al., Nat. Biotechnol. 24 (11):1392 (2006); McLean, et al., Stem Cells 25 (1):29 (2007)). To determine if brief Activin A exposure of the cells limited to one day could promote mesoderm formation and cardiogenesis rather than endoderm, varying concentrations of Activin A in defined media (RPMI with B27 without insulin supplement) was added to cell cultures with a matrix overlay to enhance growth factor delivery. Exposure to Activin A for one day resulted in areas of contracting sheets of cardiomyocytes by day 8.

Flow cytometry was conducted to determine dose-dependent effects of Activin A. Cells were detached from 6-well or 12-well plates by first washing cells in PBS at room temperature. Cells were then incubated in 1 ml/well 0.25% trypsin-EDTA (Invitrogen) plus 2% chick serum (Sigma) for 5 minutes at 37° C. Cell aggregates were disrupted by pipetting up and down and trypsin was neutralized using equal volume of EB20 medium. Cells were centrifuged 5 minutes at 1000 rpm, the supernatant discarded, and the pellet was resuspended in 1 ml 1% paraformaldehyde for fixation. Samples were incubated 10 minutes in a 37° C. water bath in the dark. Samples were centrifuged, pellets were resuspended in 1 ml ice-cold 90% methanol, and incubated on ice for 30 minutes to permeabilize the cells. Cells were washed once in FACS buffer (PBS without Ca/Mg$^{2+}$, 0.5% BSA, 0.1% NaN$_3$) plus 0.1% Triton, centrifuged, and supernatant discarded leaving about 50 µl. Samples were transferred to flow cytometry tubes for labeling. Primary antibodies were diluted in 50 µl/sample FACS buffer plus 0.1% Triton and aliquoted to each sample for a total sample volume of 100 µl. Samples were incubated overnight at 4° C. Mouse monoclonal anti-Oct4 (IgG$_{2b}$, Santa Cruz Biotechnology, 1:100 dilution) and rabbit polyclonal anti-Nanog (IgG, 1:100 dilution, Cosmo Bio Co Ltd) were used to stain for pluripotency markers, mouse monoclonal anti-human cTnT (IgG$_1$, Thermo Scientific, 1:200 dilution) was used to stain for a cardiac marker, mouse monoclonal anti-human Ki-67 (IgG$_1$, BD, 1:100 dilution) was used for proliferation measurements, mouse monoclonal anti-human/mouse cleaved caspase-3 (Asp175) antibody (R&D, 10 ug/ml) was used for apoptosis measurements, and mouse monoclonal anti-mouse p16 antibody (Santa Cruz, 1:500 dilution) was used for cell senescence measurement. Cells were washed twice in 3 ml FACS buffer plus 0.1% Triton, centrifuged, and supernatant discarded leaving ~50 µl. Secondary antibody specific to the primary IgG isotype was diluted 1:500 in 50 µl/sample FACS buffer plus Triton and aliquoted to each sample (final sample volume 100 µl). Samples were incubated for 30 minutes in the dark at room temperature, washed twice in FACS buffer plus Triton. Samples were centrifuged, resuspended in 300-500 µl FACS buffer plus Triton and stored on ice until analysis. Data were collected on a FACSCaliber flow cytometer (Beckton Dickinson) and analyzed using FlowJo software.

Figure 8A:
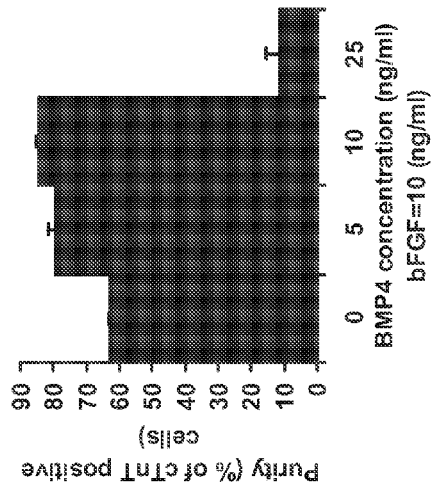
FIG. 8A-D illustrate cell culture exposure to various concentrations of Activin A, BMP4, and bFGF.
Figure 8C:
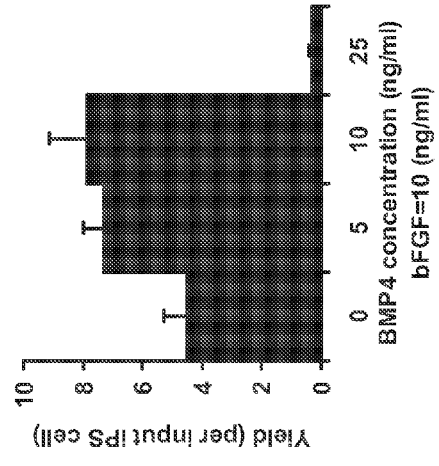
Figure 8B:
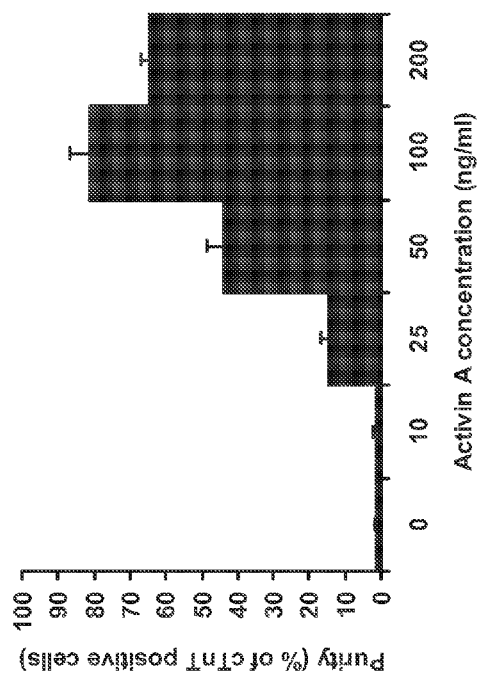
Figure 8D:
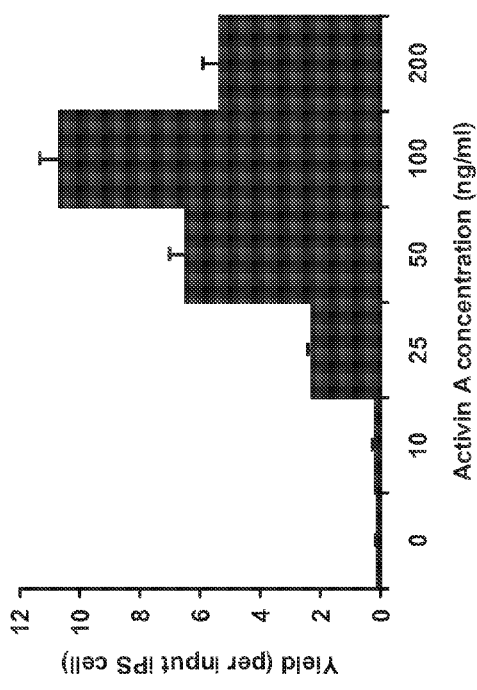
Figure 9:
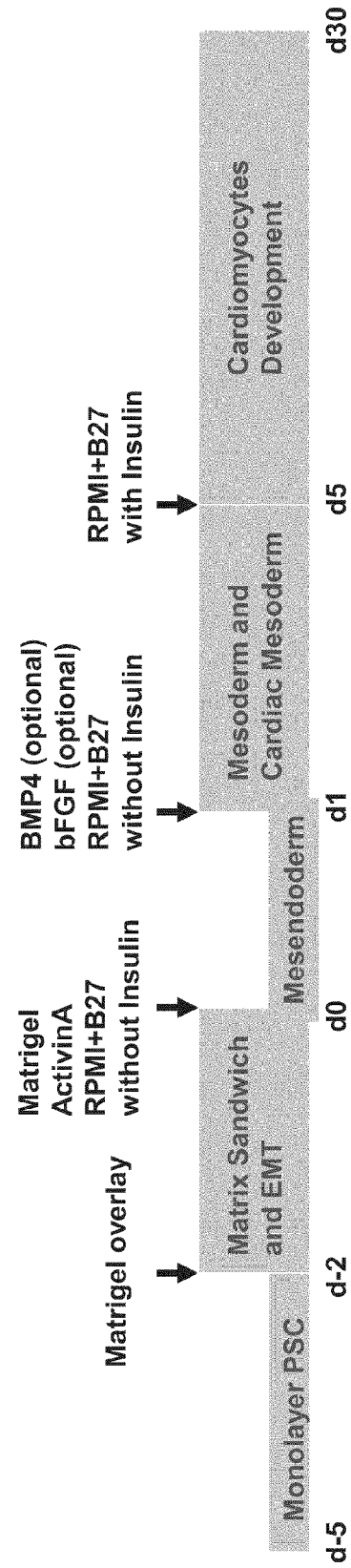
FIG. 9 illustrates an exemplary protocol.

Flow cytometry evaluation demonstrated a dose-dependent effect of Activin A. Exposure for one day with 100 ng/ml of Activin A resulted in approximately 80% of cTnT-positive cardiomyocytes at day 15 (FIG. 8A). Cardiomyocyte yield per input iPS cell was similarly Activin A concentration-dependent with a maximal yield of 11 cTnT-positive cardiomyocytes per starting iPS cells with 100 ng/ml of Activin A (FIG. 8B). To increase yield and purity of the cardiomyocytes, BMP4 and bFGF were added at day 1-5 after Activin A exposure for 1 day. At 5 ng/ml bFGF, a concentration of 10 ng/ml of BMP4 maximally increased both the percentage and yield of cTnT-positive cardiomyocytes whereas 25 ng/ml of BMP4 strongly inhibited cardiogenesis (FIGS. 8C and D). The schematic of FIG. 9 schematically summarizes a preferred protocol of growth factor administration, i.e., adding Activin A for one day followed by BMP4 and bFGF for 4 days, but other administration schedules were suitable. Various combinations of media containing or free of insulin were also tested, as shown in Table 1.

TABLE 1

Media supplementation protocol.

| Day 0-1 | Day 1-5 |
|---|---|
| Complete B-27 | Complete B-27 |
| Complete B-27 | B-27 without insulin |
| B-27 without insulin | Complete B-27 |
| B-27 without insulin | B-27 without insulin |

In some experiments, insulin was added to RPMI with B27 serum free supplement. Insulin appeared to adversely affect cardiogenesis in 19-9-11 cell lines when added to the culture medium at a concentration of 100 ng/ml from day 0-5. Insulin-containing medium RPMI with B27 complete supplement also reduced cardiogenesis of H1; IMR90 iPS; 19-9-11 iPS; and 6-9-9 iPS cells. Other media, such as DMEM/F12 with B27 insulin-free supplement, also supported cardiogenesis.

Figure 10:
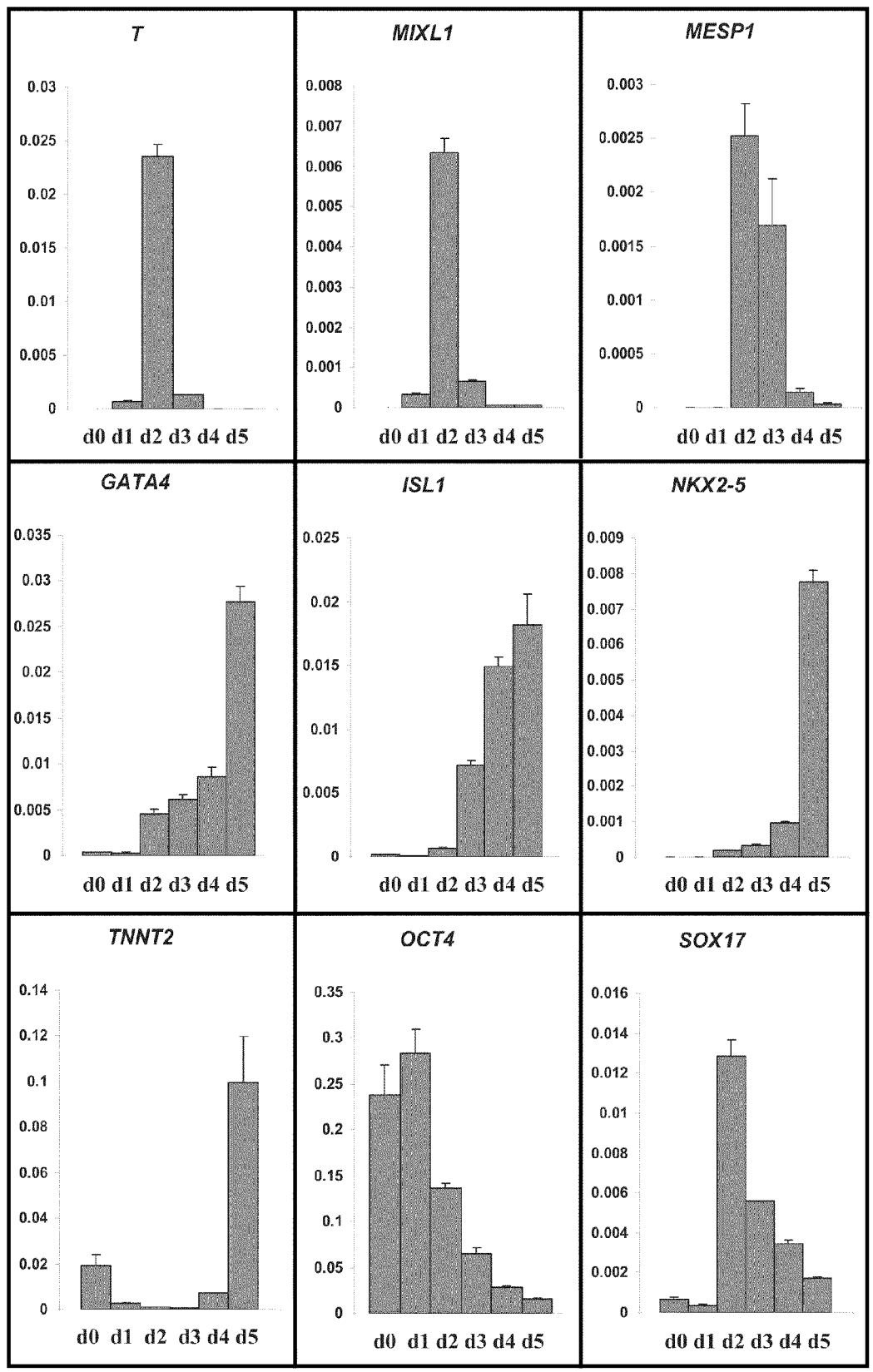
FIG. 10 illustrates the time-course of gene expression at days 0-5 during differentiation assessed by quantitative RT-PCR.

To determine the time-course of gene expression during differentiation, quantitative RT-PCR was performed, essentially as described in Example 3, at days 1-5 of culture (FIG. 10). RT-PCR was performed to monitor gene expression at days 0, 2, 5, 7, 9, 12, 15, 20, and 30. These analyses demonstrated sequential up-regulation of primitive streak genes T, MIXL1, and MESP1, followed by expression of the mesoderm and cardiac transcription factors GATA4, ISL1, and NKX2-5, and, eventually, the cardiac myofilament proteins TNNT2, TNNI3, MYL7, and MYL2. Conversely, expression of the pluripotency markers OCT4 and NANOG was progressively down-regulated. Furthermore, the differentiated cell population did not express neuroectoderm (SOX1 and PAX6) and definitive endoderm (FOXA2) genes. Immunolabeling for cTnT revealed large cardiomyocyte networks. Cardiomyocytes isolated from these networks exhibited sarcomeric organization, as assessed by immunolabeling of the myofilament proteins α-actinin and MLC2a. After 15 days of differentiation, 40-80% of the cells were cTnT-positive cardiomyocytes, compared to only 0.3-3.0% cTnT-positive cardiomyocytes when traditional EB differentiation protocols were used. Functional electrophysiology analysis determined that the iPS cell-derived cardiomyocytes using the described method exhibited similar properties as ES cell-derived cardiomyocytes.

Similar efficient cardiac differentiation using the matrix overlay method was obtained using several different iPS cell lines, including virally-generated iPS cells, and vector- and transgene-free iPS cells, as well as human ES cell lines. To determine if iPS cell-derived cardiomyocytes exhibit similar expansion during in vitro differentiation compared to cardiomyocytes generated from ES cells, flow cytometry analysis was performed during in vitro differentiation. Cells were co-labeled with antibodies specific to the cardiac markers MF20 and Ki-67 at day 15 and 30 after differentiation. The vector and transgene-free iPS cells lines showed similar proliferation to ES cell lines at day 15, but the lentiviral-generated iPS cell line (IMR90 C4) proliferated less (40.2±3.0%). None of the cardiomyocytes exhibited signs of senescence or apoptosis, assessed by flow cytometric analysis of p16 and cleaved caspase-3, at day 30 in vitro differentiation of iPS and ES cell lines (iPS DF6-9-9T, iPS DF19-9-11T, IMR90 C4 and H1).

Example 5

Transplantation of iPS Cell-Derived Cardiomyocytes

To determine if pluripotent stem cell-derived cardiomyocytes can be used for transplantation to treat degenerative heart disease, a skin window cardiac graft model was developed to dynamically follow transplanted pluripotent stem cell-derived cardiomyocytes in vivo and to compare cardiomyocyte grafts derived from ES and iPS cells.

Dorsal skin fold window chambers were surgically created in female, eight week-old NOD/SCID/IL-2rg null mice (The Jackson Laboratory). For cell sample preparation and transplantation, contracting cardiomyocyte clusters were microdissected and embedded in 100 µl growth factor-reduced MATRIGEL® at a final concentration of 4.3 mg/mL. Cardiomyocyte-MATRIGEL® samples were solidified at room temperature for 20 minutes, and transplanted into the window chambers. Each sample contained approximately $2 \times 10^6$ cells.

Live imaging of the CM-grafts in the skin window chambers was performed dynamically for 4 weeks using microscopy and LEICA-80 software. After four weeks, grafts in mouse host tissue were isolated, embedded in OTC, and frozen at −80° C. The samples were then sectioned into 5 µm tissue sections, stained with Hematoxylin & Eosin (H&E), and subjected to histopathologic analysis. Some sections were double stained for cardiomyocytes (Troponin-T, Thermo Scientific and MF-20), apoptosis (cleaved Caspase-3, R&D Systems), proliferation (Ki-67, BD) and senescence (p16, Santa Cruz)-markers and detected with immunofluorescence.

Transplanted iPS- and ES cell-derived cardiomyocytes were readily visible by microscopy in the window chambers after transplantation and the cells contracted visibly. ES- and iPS cell-derived cardiomyocyte tissue grafts increased over the 4 weeks of analysis to a comparable extent. The cells form contracting, vascularized grafts that survive for at least 30 days and no tumors were observed. Inspection of HE-stained graft-chamber tissue sections after 4 weeks revealed large areas of tissue grafts (FIG. 4C). Quantitative measurements of immunohistochemical staining showed similar number of cTnT-positive cells in the grafted cardiomyocytes derived from iPS and ES cells. Thus, iPS- and ES cells-derived cardiomyocytes can survive for an extended period following in vivo transplantation.

To examine proliferation, senescence, and apoptosis of the grafted cardiomyocytes in vivo, graft-chamber tissue sections were co-labeled for the cardiac marker MF20 with Ki-67, p16, and cleaved caspase-3. After surviving for 4 weeks in vivo, 11-15% of the cardiomyocytes were Ki-67 positive, 25-32% of the cardiomyocytes were p16 positive, and only 0.4-1.5% cardiomyocytes showed signs of apoptosis. Thus, the matrix overlay method produced cell populations suitable for transplantation into an animal.

SEQUENCE LISTING

Not applicable.

We claim:

1. A method for culturing pluripotent stem cells to obtain foci of cells undergoing an epithelial-to-mesenchymal transition, the method comprising the steps of:
   providing pluripotent stem cells as a monolayer on a support;
   applying a matrix layer to the apical surface of pluripotent stem cells of the monolayer, wherein both the support and the matrix layer contact the pluripotent stem cells; and
   culturing the pluripotent stem cells contacted by the matrix layer to induce the contacted pluripotent stem cells to form multilayered foci of cells undergoing the epithelial-to-mesenchymal transition, wherein culturing comprises providing Activin A to the pluripotent stem cells contacted by the matrix layer, and wherein cells undergoing the epithelial-to-mesenchymal transition comprise N-cadherin-positive mesenchymal cells.

2. The method of claim 1, further comprising the step of culturing the foci to form a differentiated cell population comprising cardiomyocytes.

3. The method of claim 1, wherein Activin A is provided in the matrix layer.

4. The method of claim 1, wherein culturing comprises providing 100 ng/ml Activin A and at least one factor selected from the group consisting of 0-10 ng/ml BMP4 and 0-25 ng/ml bFGF to the pluripotent stem cell.

5. The method of claim 1, wherein the Activin A is provided to the pluripotent stem cells for only one day.

6. The method of claim 1, wherein the matrix layer comprises extracellular matrix proteins.

7. The method of claim 1, wherein the pluripotent stem cells are cultured in defined medium.

8. The method of claim 7, wherein the defined medium comprises a serum-free growth supplement.

9. The method of claim 7, wherein the defined medium is substantially free of insulin.

10. The method of claim 7, further comprising the step of adding insulin to the defined medium on day 5 of culture.

11. The method of claim 2, wherein the differentiated cell population comprises 30-90% cardiac troponinT (cTnT)-positive cardiomyocytes.

12. The method of claim 1, wherein the foci have a mean diameter of about 100 μm to about 200 μm.

13. The method of claim 1, wherein the cells do not form embryoid bodies.

14. The method of claim 1, further comprising the step of detecting a mesenchymal marker.

15. The method of claim 14, wherein the marker is N-cadherin surface expression.

16. The method of claim 1, further comprising the step of contacting the pluripotent stem cells to an agent that modulates foci formation.

17. A culture composition comprising:
   a support;
   a monolayer of pluripotent stem cells on the support;
   a matrix layer, wherein the support and the matrix layer contact the monolayer of pluripotent stem cells, wherein the matrix layer contacts the apical surface of pluripotent stem cells of the monolayer, and wherein at least some of the pluripotent stem cells form multilayered foci comprising N-cadherin-positive cells.

18. A method for administering in vitro-generated cardiomyocytes to a human or non-human animal, the method comprising the steps of:
   providing a monolayer of pluripotent stem cells on a support in vitro;
   applying a matrix layer to the apical surface of pluripotent stem cells of the monolayer, wherein both the support and the matrix layer contact the pluripotent stem cells;
   culturing pluripotent stem cells contacted by the matrix layer in vitro to form a differentiated cell population comprising cardiomyocytes, wherein culturing comprises providing Activin A to the pluripotent stem cells contacted by the matrix layer; and
   administering cardiomyocytes from the differentiated cell population to the human or non-human animal.

19. The method of claim 18, wherein cardiomyocytes from the differentiated cell population are administered to the heart of the human or non-human animal.

20. A method of producing cardiomyocytes, the method comprising the steps of:
   (a) providing vector-free iPS cells in a monolayer on a support in vitro;
   (b) applying a matrix layer to the apical surface of the vector-free iPS cells, wherein both the support and the matrix layer contact the vector-free iPS cells;
   (c) culturing the vector-free iPS cells contacted by the matrix layer in vitro whereby the vector-free iPS cells differentiate to form cardiomyocytes, wherein culturing comprises providing Activin A to the pluripotent stem cells contacted by the matrix lam; and
   (d) isolating the cardiomyocytes from the vector-free iPS cell culture to obtain a population of cardiomyocytes.

21. The method of claim 1, further comprising providing at least one factor selected from the group consisting of bone morphogenetic protein 4 (BMP4) and basic fibroblast growth factor (bFGF) to the pluripotent stem cells contacted by the matrix layer.

22. The method of claim 21, wherein the Activin A and the at least one factor selected from the group consisting of bone morphogenetic protein 4 (BMP4) and basic fibroblast growth factor (bFGF) are added sequentially.

23. The method of claim 21, wherein the at least one factor is provided in the matrix layer.

* * * * *